United States Patent [19]

Andrade et al.

[11] Patent Number: 4,691,062
[45] Date of Patent: Sep. 1, 1987

[54] PROCESS FOR THE PRODUCTION OF 4-CHLORO-BUTANALS

[75] Inventors: Juan Andrade, Kleinostheim; Gunter Prescher, Hanau; Klaus Kohler, Hainburg, all of Fed. Rep. of Germany

[73] Assignee: Degussa Aktiengesellschaft, Frankfurt am Main, Fed. Rep. of Germany

[21] Appl. No.: 921,474

[22] Filed: Oct. 22, 1986

[30] Foreign Application Priority Data

Oct. 24, 1985 [DE] Fed. Rep. of Germany ....... 3537815

[51] Int. Cl.$^4$ ............................................. C07C 45/42
[52] U.S. Cl. .................................. 568/495; 568/465; 568/490; 568/676
[58] Field of Search .............. 568/465, 495, 496, 676, 568/490

[56] References Cited

U.S. PATENT DOCUMENTS 2,579,515 12/1951 Roach ................................ 568/676
3,093,689  6/1963 Cofer et al. ........................ 568/676
4,551,560 11/1985 Rizkalla .............................. 568/676

FOREIGN PATENT DOCUMENTS 677569   1/1974 Canada ............................... 568/676
109441   6/1983 Japan ................................. 568/676
0159437  9/1983 Japan ................................. 568/495
355143  12/1970 U.S.S.R. ........................... 568/676

Primary Examiner—Werren B. Lone
Attorney, Agent, or Firm—Cushman, Darby & Cushman

[57] ABSTRACT 4-chloro-butanals of the formula

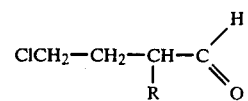

where R is hydrogen or a straight or branched chain alkyl group of 1 to 4 carbon atoms are produced by reacting the corresponding 1,1-dimethoxy-4-hydroxybutane at a temperature between −20° and +80° C. in the presence of triphenylphosphine with carbon tetrachloride and hydrolyzing the 1,1-dimethoxy-4-chlorobutane obtained in acid medium.

6 Claims, No Drawings

PROCESS FOR THE PRODUCTION OF 4-CHLORO-BUTANALS

RELATED CASE

Andrade application, Ser. No. 921,473 filed on Oct. 22, 1986, and corresponding to German patent application No. P3537813.1 is directed to using the 4-chloro-2-methyl-butanal produced in the present invention to prepare 1-methylcyclopropanecarboxaldehyde.

BACKGROUND OF THE INVENTION

The invention is directed to a process for the production of 4-chloro-butanals of the formula

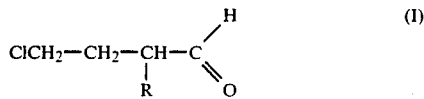

in which R is hydrogen or a straight or branched chain alkyl group having 1 to 4 carbon atoms, e.g., methyl, ethyl, propyl, isopropyl, n-butyl, sec.butyl or t-butyl. The 4-chloro-butanals of formula (1) can be condensed with salicylhydroxamic acid, which optionally can be substituted, to form 2,3,4,4a-tetrahydro-1OH-1,2-oxazino-[3,2-b]-[1,3]-benzoxazin-10-ones (cf. Arzneim.-Forsch. Drug Res. 27(I), No. 4 (1977), page 760). (S)-4-chloro-2-methyl-butanal furthermore is an important intermediate product for the production of synthetic vitamin E. (see German OS No. 2720775).

It is already known to produce 4-chlorobutanal by hydrogenation of 4-chloro-butyric acid chloride in the presence of a poisoned noble metal catalyst (J. Am. Chem. Sec. Vol. 73 page 1365 (1951)) or in the presence of an alloy catalyst (German OS No. 2506157), yield of 4-chloro-butanal, however, by these known processes is relatively poor.

SUMMARY OF THE INVENTION

The present invention is directed to a process of producing a 4-chloro-butanal of formula (I) by (a) reacting a 1,1-dimethoxy-4-hydroxy-butane of the formula

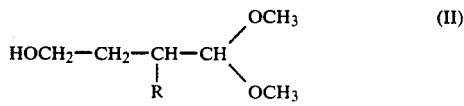

in which R is as defined above, at a temperature between −20° and +80° C. in the presence of 0.1 to 20 times the molar amount of triphenylphosphine with the 1.0 to 10 fold molar amount of carbon tetrachloride and (b) hydrolyzing the 1,1-dimethoxy-4-chlorobutanal of the formula

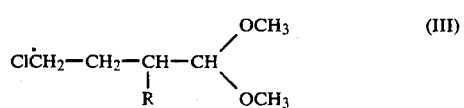

formed in reaction step (a) and wherein R is defined above, in known manner in acid medium.

Through this reaction sequence 4-chlorobutanals of formula (I) can be produced in a simple manner and in good yield.

The 1,1-dimethoxy-4-hydroxy-butane of formula (II) serving as starting material in reaction step (a) can be readily produced by hydroformylation of acrolein dimethylacetal, optionally substituted in the 2-position, and subsequent hydrogenation of the formyl group.

Reaction step (a) is preferably carried out at a temperature between +20° and +70° C. The triphenylphosphine is preferably in 1 to 2 fold molar amounts, the carbon tetrachloride preferably in 1 to 10 fold molar amounts. The process is suitably carried out in such manner that the 1,1-dimethoxy-4-hydroxy-butane of formula (I) is slowly dropped into a solution of the triphenylphosphine in the carbon tetrachloride.

It is especially advantageous if the carbon tetrachloride additionally contains a tertiary amine having a boiling point below 100° C./1 bar and a tertiary amine having a boiling point over 200° C./1 bar. The lower boiling tertiary amine is suitably used in an amount between 0.001 and 0.1 part by weight, the higher boiling tertiary amine in an amount between 0.05 and 0.7 part by weight, in each case per part by weight of the 1,1-dimethoxy-4-hydroxy-butane of formula (II) employed. Suitable lower boiling tertiary amines for example are methyldiethyl amine and preferably triethylamine, suitable higher boiling tertiary amines are tri-n-butylamine, N-methyl indole, isoquinoline and preferably quinoline.

During the reaction a white precipitate of triphenylphosphine oxide forms. After the end of the addition of the 1,1-dimethoxy-4-hydroxy-butane of formula (II) suitably the reaction mixture is stirred for a further 2 to 3 hours and then filtered at room temperature. The filtrate is concentrated to a smaller volume and the 1,1-dimethoxy-4-chlorobutane of formula (III) formed is fractionally distilled under reduced pressure.

Reaction step (b) is suitably carried out at a temperature between 20° and 60° C. It takes place in known manner in acid medium, that is in the presence of a strongly acidic ion exchanger or preferably a mineral acid, expecially dilute sulfuric acid. For example, the procedure can be such that 1,1-dimethoxy-4-chlorobutane of formula (III) is treated under vigorous stirring with excess dilute aqueous sulfuric acid. Then after 2 to 3 hours the reaction mixture is extracted with methylene chloride. The combined methylene chloride phases are washed with sodium carbonate solution and with water and dried over magnesium sulfate. After filtering off the magnesium sulfate the methylene chloride is evaporated and the residue is fractionally distilled under reduced pressure.

The invention will be explained in more detail through the following examples.

The process can comprise, consist essentially of or consist of the recited steps with the started materials.

DETAILED DESCRIPTION

Example 1

129 grams (0.96 mole) of 1,1-dimethoxy-4-hydroxy-butane were slowly dropped into a solution of 315 grams (1,2 moles) of triphenylphosphine, 67.2 grams of quinoline and 2.9 grams of triethylamine in 362 ml of carbon tetrachloride at 20° C. with cooling.

After the end of the addition, the temperature increased during the post reaction to about 60° C., whereby triphenylphosphine oxide gradually fell out as a white precipitate. The reaction mixture was stirred for a further two hours, cooled to 20° C. and filtered. The filtrate was then distilled under reduced pressure at 18 mbar. The desired 1,1-dimethoxy-4-chloro-butane passed over at 68° C. The yield, based on the 1,1-dimethoxy-4-hydroxy-butane employed was 123 grams or 84% of theory.

This was dropped into 1 liter of 0.2N sulfuric acid at 50° C. and stirred further for two hours. After cooling to 20° C. the organic phase was separated off, the aqueous phase extracted 3 times, each time wth 200 ml of methylene chloride, the combined organic phases washed neutral with sodium carbonate solution, dried over magnesium sulfate and distilled at 50 mbar. The desired 4-chloro-butanal passed over at 74° C. The yield was 80 grams or 93% of theory.

Example 2

74 grams (0.5 mole) of 1,1-dimethoxy-2-methyl-4-hydroxy-butane were dropped into a solution of 157.5 grams (0.6 mole) of triphenylphosphine, 34 grams of quinoline and 1.5 grams of triethylamine in 181 ml of carbon tetrachloride at 40° C., whereby gradually triphenylphosphine oxide fell out, the reaction mixture was stirred for another two hours at 40° C., and then the procedure was as in EXAMPLE 1. The yield of 1,1-dimethoxy-2-methyl-4-chlorobutane, based on the 1,1-dimethoxy-2-methyl-4-hydroxy-butane, was 64.9 grams (78% of theory) having a boiling point of 73° C. at 20 mbar. This was then hydrolyzed as in EXAMPLE 1 to 4-chloro-2-methyl-butanal. Yield 44.4 grams (94.7% of theory) having a boiling point of 76° to 78° C. at 40 mbar.

Example 3

The procedure was as in EXAMPLE 1 but there were employed 33.5 grams (0.25 mole) of 1,1-dimethoxy-4-hydroxy-butane, 78.7 grams (0.3 mole) of triphenylphosphine, 3.4 grams of quinoline, 3.4 grams of triethylamine and 240 ml of carbon tetrachloride. The yield of 4-chloro-butanal based on the 1,1-dimethoxy-4-hydroxy-butane, was 21 grams or 79% of theory.

Example 4

The procedure was as in EXAMPLE 2 except that there were employed 370 grams (2.5 moles) of 1,1-dimethoxy-2-methyl-4-hydroxy-butane, 787 grams (3 moles) of triphenylphosphine, 220 grams of quinoline and 33 grams of triethylamine in 2 liters of carbon tetrachloride. The yield of 4-chloro-2-methyl-butanal, based on the 1,1-dimethoxy-2-methyl-4-hydroxy-butane employed, was 244 grams or 81% of theory.

The entire disclosure of German priority application No. P.3537815.8 is hereby incorporated by reference.

It is claimed:

1. A process for the production of a 4-chloro-butanal of the formula

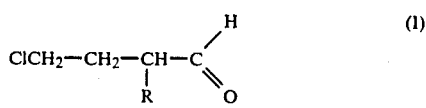

wherein R is hydrogen or a 1 to 4 carbon atom alkyl comprising
    (a) reacting a 1,1-dimethoxy-4-hydroxybutane of the formula

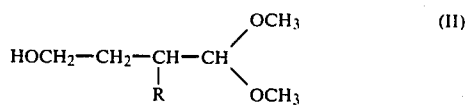

at a temperature between −20° and +80° C. with a 1.0 to 10 fold molar amount of carbon tetrachloride in the presence of a 0.1 to 20 fold molar amount of triphenylphosphine and
    (b) hydrolyzing in acid medium the 1,1-dimethoxy-4-chloro-butane formed of the formula

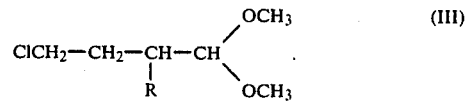

2. A process according to claim 1 wherein reaction step (a) is carried out in the presence of both (1) a tertiary amine having a boiling point below 100° C./1bar and (2) a tertiary amine having a boiling point above 200° C./1 bar.

3. A process according to claim 2 wherein the lower boiling tertiary amine is employed in an amount between 0.001 and 0.1 part by weight per part by weight of 1,1-dimethoxy-4-hydroxy-butane employed of formual (II).

4. A process according to claim 3 wherein the higher boiling tertiary amine is employed in an amount between 0.05 and 0.7 part by weight per part by weight of 1,1-dimethoxy-4-hydroxy-butane employed of formula (II).

5. A process according to claim 2 wherein the higher boiling tertiary amine is employed in an amount between 0.05 and 0.7 part by weight per part by weight of 1,1-dimethoxy-4-hydroxy-butane employed of formula (II).

6. A process according to claim 2 wherein there is employed as the lower boiling tertiary amine triethylamine and as the higher boiling tertiary amine quinoline.

* * * * *